United States Patent
Liu et al.

(10) Patent No.: US 9,051,236 B2
(45) Date of Patent: Jun. 9, 2015

(54) METHOD FOR IMPROVING THE QUALITY OF ETHYLENE GLYCOL PRODUCTS

(75) Inventors: Juntao Liu, Shanghai (CN); Yuhong Zhang, Shanghai (CN); Wanmin Wang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 19 days.

(21) Appl. No.: 14/000,878

(22) PCT Filed: Feb. 24, 2012

(86) PCT No.: PCT/CN2012/000240
§ 371 (c)(1),
(2), (4) Date: Aug. 22, 2013

(87) PCT Pub. No.: WO2012/113269
PCT Pub. Date: Aug. 30, 2012

(65) Prior Publication Data
US 2013/0331618 A1    Dec. 12, 2013

(30) Foreign Application Priority Data
Feb. 25, 2011   (CN) .......................... 2011 1 0045250

(51) Int. Cl.
C07C 27/04      (2006.01)
C07C 29/149     (2006.01)
C07C 29/90      (2006.01)

(52) U.S. Cl.
CPC ............... C07C 29/149 (2013.01); C07C 29/90 (2013.01)

(58) Field of Classification Search
CPC ...... C07C 29/90; C07C 29/149; C07C 31/202
USPC ....................................................... 568/864
See application file for complete search history.

(56) References Cited

U.S. PATENT DOCUMENTS

| 4,762,817 A | * | 8/1988 | Logsdon et al. ............. 502/329 |
| 6,242,655 B1 | | 6/2001 | Husain |
| 6,603,048 B1 | | 8/2003 | Corbin et al. |
| 6,770,790 B1 | | 8/2004 | Li et al. |
| 8,129,548 B2 | | 3/2012 | Wood et al. |

FOREIGN PATENT DOCUMENTS

| CN | 1377333 A | | 10/2002 |
| CN | 1860090 A | | 11/2006 |
| CN | 1895766 | * | 1/2007 |
| CN | 101052607 A | | 10/2007 |
| CN | 101058526 | * | 10/2007 |
| CN | 101058526 A | | 10/2007 |
| CN | 101928201 A | | 12/2010 |
| WO | WO 99/58483 A1 | | 11/1999 |

OTHER PUBLICATIONS

CN101058526, 2007, machine translation from Espacenet on Oct. 22, 2014.*
CN1895766, 2007, machine translation from Espacenet on Oct. 22, 2014.*
Chen (CN101058526, 2007, machine translated).*
International Search Report (PCT/ISA/210) issued on May 31, 2012, by the China Patent Office as the International Searching Authority for International Application No. PCT/CN2012/000240.
Office Action issued Apr. 21, 2014, by the State Intellectual Property Office of People's Republic of China in corresponding Chinese Patent Application No. 201110045250.3. (5 pages).
Office Action issued Oct. 11, 2013, by the State Intellectual Property Office of People's Republic of China in corresponding Chinese Patent Application No. 201110045250.3. (4 pages).

* cited by examiner

*Primary Examiner* — Yevegeny Valenrod
*Assistant Examiner* — Blaine G Doletski
(74) *Attorney, Agent, or Firm* — Buchanan Ingersoll & Rooney PC

(57) ABSTRACT

A method for improving the quality of ethylene glycol products, which mainly solves the technical problem of low UV-light transmittance of the ethylene glycol products present in the prior art. The method successfully solves the problem by use of the technical solution wherein the ethylene glycol raw material and hydrogen are passed through a rotating packed bed reactor loaded with solid oxide catalyst at a temperature of about 20 to about 280° C., a pressure of about 0.1 to about 4.0 MPa, a space velocity of about 0.2 to about 100.0 $hr^{-1}$ and a molar ratio of hydrogen to ethylene glycol of from about 0.01 to 40:1, and ethylene glycol is obtained after the reaction. The solid oxide catalyst is at least one of copper-based, nickel-based and palladium-based catalysts, and the rotation rate of the rotating packed bed reactor is about 300 to about 5000 rpm.

14 Claims, No Drawings

METHOD FOR IMPROVING THE QUALITY OF ETHYLENE GLYCOL PRODUCTS

TECHNICAL FIELD

The present invention relates to a method for improving the quality of ethylene glycol products, in particular a method for improving the quality of the ethylene glycol products obtained by the hydrogenation of oxalates, preferably the hydrogenation of dimethyl oxalate or diethyl oxalate.

BACKGROUND TECHNOLOGY

Ethylene glycol (EG) is an important organic chemical raw material, which is mainly used for producing polyester fibers, antifreezes, unsaturated polyester resins, lubricants, plasticizers, non-ionic surfactants and explosives etc. In addition, ethylene glycol can also be used in such fields as coating, photographic developer, brake fluid and ink, as the solvent and medium of ammonium perborate and for producing special solvents like glycol ether. Ethylene glycol has a wide range of uses, including a very important use as the basic raw material for producing the polyester(PET) of polyester fibers, Ethylene glycol here being generally referred to as the fiber-grade ethylene glycol product.

At present, both domestic and foreign large-scale ethylene glycol productions mainly adopt the oil route, i.e., direct hydration or pressure hydration process route. According to said process, ethylene oxide and water are compounded to a mixed aqueous solution by 1:20~22 (molar ratio); said mixed aqueous solution reacts in a fixed bed reactor for 18~30 minutes at 130~180° C. and 1.0~2.5 MPa; ethylene oxide is completely converted into mixed alcohol; and the resultant ethylene glycol aqueous solution has a content of about 10% (by mass); ethylene glycol is then obtained by dehydration concentration and vacuum rectification separation using a multi-effect evaporator. However, the production device requires the installation of multiple evaporators and consumes a large quantity of energy used for dehydration, which results in long running of the production process, more equipments and high energy consumption.

Currently, from a global point of view, the oil resource is increasingly in short supply. Moreover, the world sees great oil price fluctuations. The pattern of the resources in China can be summarized as having less oil, less gas, and more coal. The development of C1 chemical industry, which can not only make full use of the natural gas and coal resources and reduce the dependence on oil imports, but also can reduce the pressure on the environment, is a very important area for research. It is a quite attractive coal chemical industry route to prepare oxalate using carbon monoxide as the raw material and then prepare ethylene glycol by hydrogenating oxalate. Nowadays, both domestic and foreign researches into preparing ethylene glycol by using carbon monoxide as the raw material have achieved excellent effects. The industrial production thereof has been mature. However, as regards the preparation of ethylene glycol by the hydrogenation of oxalate, there is still more work needing further research, especially the hydrogenation of oxalate, wherein more byproducts are produced, and the existence of trace amounts of unsaturated double bond-containing compounds will affect the quality of the ethylene glycol products. One important index for measuring the quality of the fiber-grade ethylene glycol products is the UV-light transmittance at 220 nm, because it will affect the luster and chrominance of the downstream polyester products. As regards the ethylene glycol produced by the oil route, it is generally considered that the important factors affecting the UV-light transmittance at 220 nm of the fiber-grade ethylene glycol products are the aldehyde-containing byproducts present in the products. As for the ethylene glycol products produced by the hydrogenation of oxalate, it is generally believed that the important factor affecting the UV-light transmittance at 220 nm of the ethylene glycol products is different from that of the oil route; generally, less aldehyde-containing byproducts are produced; other non-aldehyde carbonyl compounds may be the important factors affecting the UV-light transmittance at 220 nm of the ethylene glycol products.

The prior art usually uses ion exchange resin as the catalyst to refine and purify ethylene glycol, e.g., U.S. Pat. No. 6,242,655 describes a method of using a strongly acidic cation exchange resin as the catalyst, wherein after the treatment, the content of the aldehyde group in the ethylene glycol products decreases from 20 ppm to 5 ppm or less. However, the defect of the existing method is that the content of the aldehyde group in the ethylene glycol products can only be removed to about 2 ppm at most, but the UV-light transmittance at 220 nm of the ethylene glycol products at this moment still does not reach a very ideal value. Meanwhile, the existing method only applies to ethylene glycol products of the oil routes. The effect of said method on the coal-based products has not been reported. Therefore, how to improve the UV-light transmittance of the coal-based ethylene glycol products and further guarantee the quality of the products is a very important research subject. At present, literature or report on said subject is seldom disclosed.

SUMMARY OF THE INVENTION

The technical problem to be solved by the present invention is to provide a novel method for improving the quality of the ethylene glycol products, thereby overcoming the problem of low UV-light transmittance of the ethylene glycol products present in the prior art. The ethylene glycol products obtained by said method have high UV-light transmission among other advantages.

To this end, the present invention adopts the following technical solution: a method for improving the quality of ethylene glycol products, wherein the ethylene glycol raw material and hydrogen are passed through the rotating packed bed reactor loaded with solid oxide catalyst at a temperature of about 20 to about 280° C., a pressure of about 0.1 to about 4.0 MPa, a space velocity of about 0.2 to about 100.0 hr$^{-1}$ and a molar ratio of hydrogen to ethylene glycol of from about 0.01 to 40:1, and ethylene glycol is obtained after the reaction, wherein said solid oxide catalyst is selected from at least one of copper-based, nickel-based and palladium-based catalysts, and the rotation rate of said rotating packed bed reactor is about 300 to about 5000 rpm.

In one embodiment, said temperature is about 30 to about 260° C., the pressure is about 0.3 to about 3.0M Pa, the space velocity is about 1 to about 50.0 hr$^{-1}$, and the molar ratio of hydrogen to ethylene glycol is from about 0.1 to 30:1.

In another embodiment, the rotation rate range of the rotating packed bed reactor is about 500 to about 3000 rpm.

In another embodiment, the ethylene glycol raw material comes from the ethylene glycol products obtained from the hydrogenation of oxalate, and the mass concentration of the ethylene glycol raw material is preferably greater than 99%.

In another embodiment, said solid oxide catalyst has a certain intensity of about 60 to about 400N/cm, preferably in the range of from about 100 to about 300N/cm. Said intensity can be obtained by using an organic binder, where said organic binder may be for example: polyvinyl alcohol, hydroxypropyl methylcellulose, methylcellulose or hydroxypropyl methylcellulose.

Different from the prior art, the solid oxide catalyst obtained by the use of said organic binder can be used at a lower temperature in the above method. Said solid oxide catalyst may have the following parameters:

a surface area of about 10 to about 500 m$^2$/g, a pore volume of about 0.1 to about 1 ml/g, and a mean pore diameter of about 2 to about 13 nm.

Said solid oxide catalyst may be, for example, a catalyst comprising palladium oxide and/or copper oxide and/or nickel oxide.

In another embodiment, said solid oxide catalyst may contain conventional carriers and may be optionally added with conventional adjuvants. The carrier may be, for example, silica, alumina and/or molecular sieve. The solid oxide catalyst can be prepared by methods in the present technology field.

In another embodiment, said rotating packed bed reactor may, for example, use HIGEE-001 type reactor (produced by SRIPT).

As everyone knows, during the reaction process for producing ethylene glycol from the hydrogenation of oxalate, in addition to the ethylene glycol target products, certain amounts of by-products, e.g., normal amounts of ethanol, butylene glycol and propylene glycol, and other trace amounts of compounds containing unsaturated double bond, are also contained. The conventional separation methods or other special rectification methods can remove most of the compounds in normal amounts, such as ethanol and propylene glycol, etc., making the purity of the products reach more than 99.8%. However, as is often the case, although the purity of ethylene glycol is already very high, the UV-light transmittances at 220 nm, 275 nm and 350 nm of the ethylene glycol products still do not reach a very ideal value (as required by the Chinese National Standards of the superior grade of ethylene glycol products, the UV-light transmittances at 220 nm, 275 nm and 350 nm of the ethylene glycol products shall be respectively greater than 75, 95 and 98). The reason lies in that the trace impurities and even trace impurities at a ppm grade have remarkable impact on the UV-light transmittance of the products. However, said trace impurities at a ppm grade are generally hard to be removed by rectification.

The present inventors have found in the studies that copper-based, nickel and/or palladium-based catalyst, has higher removal selectivity to the trace impurities in ethylene glycol in the presence of hydrogen. In addition, taking into account the low content of the impurities that affect the UV-light transmittance of the products, the reaction process is mainly controlled by proliferation. The performance of the hydrogen dispersion has significant impact on the removal effect of the impurities. Therefore, the present invention uses the rotating packed bed as the hydrogenation reactor. The advantage that the mass transfer coefficient can be improved by a geometric proportion via using the rotating packed bed greatly strengthens the mass transfer process, finally effectively removes the impurities that affect the UV-light transmittance of the products, and remarkably improves the quality of the products.

The UV-light transmittance of the ethylene glycol products obtained by use of the technical solutions of the present invention is greater than 75 at 220 nm, greater than 95 at 275 nm, and greater than 98 at 350 nm, viz., better technical effects have been achieved.

The present invention is further illustrated by the following examples, but the present invention is not limited to these Examples.

SPECIFIC EMBODIMENTS

Example 1

Nickel solid oxide (15% of nickel oxide based on the percentage by weight of the catalyst, wherein the carrier was alumina) was used as the catalyst; the catalyst had an intensity of 100N/cm, a surface area of 200 m$^2$/g, a pore volume of 0.31 ml/g, and an average pore diameter of 5 nm; the ethylene glycol product prepared from the hydrogenation of the dimethyl oxalate was used as the raw material; hydrogen and the ethylene glycol raw material (the ethylene glycol raw material had a purity of 99.8%; the UV-light transmittance of said raw material was 2 at 220 nm, 91 at 275 nm, and 95 at 350 nm) were passed through the rotating packed bed reactor (SRIPT-HIGEE-001, hereinafter the same) at a temperature of 60° C., a pressure of 1.0 MPa, a space velocity of 20 hr$^{-1}$, and a ratio of hydrogen to ethylene glycol (hereinafter refers to the molar ratio) of 3:1 and contacted with the catalyst. The effluent of ethylene glycol was obtained after the reaction, wherein the rotation rate of the rotating packed bed reactor was 500 rpm, and the UV-light transmittance of the ethylene glycol products obtained after the hydrogenation was 78 at 220 nm, 95 at 275 nm and 100 at 350 nm.

Example 2

Nickel solid oxide (30% of nickel oxide based on the percentage by weight of the catalyst, wherein the carrier was alumina) was used as the catalyst; the catalyst had an intensity of 1.50N/cm, a surface area of 300 m$^2$/g, a pore volume of 0.4 ml/g, and an average pore diameter of 8 nm; the ethylene glycol product prepared from the hydrogenation of the dimethyl oxalate was used as the raw material; hydrogen and the ethylene glycol raw material (the ethylene glycol raw material had a purity of 99.8%; the UV-light transmittance of said raw material was 2 at 220 nm, 91 at 275 nm, and 95 at 350 nm) were passed through the rotating packed bed reactor at a temperature of 90° C., a pressure of 3.0 MPa, a space velocity of 50 hr$^{-1}$, and a ratio of hydrogen to ethylene glycol of 10:1 and contacted with the catalyst. The effluent of ethylene glycol was obtained after the reaction, wherein the rotation rate of the rotating packed bed reactor was 800 rpm, and the UV-light transmittance of the ethylene glycol products obtained after the hydrogenation was 77 at 220 nm, 96 at 275 nm and 100 at 350 nm.

Example 3

Nickel solid oxide (30% of nickel oxide based on the percentage by weight of the catalyst, wherein the carrier was silica) was used as the catalyst; the catalyst had an intensity of 110N/cm, a surface area of 400 m$^2$/g, a pore volume of 0.6 ml/g, and an average pore diameter of 3 nm; the ethylene glycol product prepared from the hydrogenation of the dimethyl oxalate was used as the raw material; hydrogen and the ethylene glycol raw material (the ethylene glycol raw material had a purity of 99.9%; the UV-light transmittance of said raw material was 0 at 220 nm, 90 at 275 nm, and 95 at 350 nm) were passed through the rotating packed bed reactor at a temperature of 40° C., a pressure of 1.0 MPa, a space velocity of 10 hr$^{-1}$, and a ratio of hydrogen to ethylene glycol of 2:1 and contacted with the catalyst. The effluent of ethylene glycol was obtained after the reaction, wherein the rotation rate of the rotating packed bed reactor was 1000 rpm, and the UV-light transmittance of the ethylene glycol products obtained after the hydrogenation was 79 at 220 nm, 97 at 275 nm and 99 at 350 nm.

Example 4

Nickel solid oxide (30% of nickel oxide based on the percentage by weight of the catalyst, wherein the carrier was ZSM-5 molecular sieve) was used as the catalyst; the catalyst had an intensity of 210N/cm, a surface area of 450 m$^2$/g, a pore volume of 0.6 ml/g, and an average pore diameter of 6 nm; the ethylene glycol product prepared from the hydrogenation of diethyl oxalate was used as the raw material; hydrogen and the ethylene glycol raw material (the ethylene glycol raw material had a purity of 99.8%; the UV-light transmittance of said raw material was 10 at 220 nm, 93 at 275 nm, and 95 at 350 nm) were passed through the rotating packed bed reactor at a temperature of 100° C., a pressure of 0.5 MPa, a space velocity of 2 hr$^{-1}$, and a ratio of hydrogen to ethylene glycol of 5:1 and contacted with the catalyst. The effluent of ethylene glycol was obtained after the reaction, wherein the rotation rate of the rotating packed bed reactor was 2000 rpm, and the UV-light transmittance of the ethylene glycol products obtained after the hydrogenation was 78 at 220 nm, 96 at 275 nm and 100 at 350 nm.

Example 5

Copper solid oxide (20% of copper oxide based on the percentage by weight of the catalyst, wherein the carrier was alumina) was used as the catalyst; the catalyst had an intensity of 80N/cm, a surface area of 180 m$^2$/g, a pore volume of 0.4 ml/g, and an average pore diameter of 4 nm; the ethylene glycol product prepared from the hydrogenation of diethyl oxalate was used as the raw material; hydrogen and the ethylene glycol raw material (the ethylene glycol raw material had a purity of 99.8%; the UV-light transmittance of said raw material was 10 at 220 nm, 93 at 275 nm, and 95 at 350 nm) were passed through the rotating packed bed reactor at a temperature of 180° C., a pressure of 0.5 MPa, a space velocity of 15 hr$^{-1}$, and a ratio of hydrogen to ethylene glycol of 20:1 and contacted with the catalyst. The effluent of ethylene glycol was obtained after the reaction, wherein the rotation rate of the rotating packed bed reactor was 1000 rpm, and the UV-light transmittance of the ethylene glycol products obtained after the hydrogenation was 79 at 220 nm, 97 at 275 nm and 100 at 350 nm.

Example 6

Copper solid oxide (10% of copper oxide based on the percentage by weight of the catalyst, wherein the carrier was silica) was used as the catalyst; the catalyst had an intensity of 130N/cm, a surface area of 250 m$^2$/g, a pore volume of 0.6 ml/g, and an average pore diameter of 7 nm; the ethylene glycol product prepared from the hydrogenation of the dimethyl oxalate was used as the raw material; hydrogen and the ethylene glycol raw material (the ethylene glycol raw material had a purity of 99.8%; the UV-light transmittance of said raw material was 0 at 220 nm, 90 at 275 nm, and 95 at 350 nm) were passed through the rotating packed bed reactor at a temperature of 240° C., a pressure of 2.0 MPa, a space velocity of 60 hr$^{-1}$, and a ratio of hydrogen to ethylene glycol of 30:1 and contacted with the catalyst. The effluent of ethylene glycol was obtained after the reaction, wherein the rotation rate of the rotating packed bed reactor was 1500 rpm, and the UV-light transmittance of the ethylene glycol products obtained after the hydrogenation was 80 at 220 nm, 97 at 275 nm and 100 at 350 nm.

Example 7

Palladium solid oxide (0.15% of palladium oxide based on the percentage by weight of the catalyst, wherein the carrier was alumina) was used as the catalyst; the catalyst had an intensity of 160N/cm, a surface area of 80 m$^2$/g, a pore volume of 0.2 ml/g, and an average pore diameter of 6 nm; the ethylene glycol product prepared from the hydrogenation of the dimethyl oxalate was used as the raw material; hydrogen and the ethylene glycol raw material (the ethylene glycol raw material had a purity of 99.8%; the UV-light transmittance of said raw material was 0 at 220 nm, 90 at 275 nm, and 95 at 350 nm) were passed through the rotating packed bed reactor at a temperature of 80° C., a pressure of 1.0 MPa, a space velocity of 10 hr$^{-1}$, and a ratio of hydrogen to ethylene glycol of 10:1 and contacted with the catalyst. The effluent of ethylene glycol was obtained after the reaction, wherein the rotation rate of the rotating packed bed reactor was 3000 rpm, and the UV-light transmittance of the ethylene glycol products obtained after the hydrogenation was 76 at 220 nm, 96 at 275 nm and 99 at 350 nm.

Example 8

The composite solid oxide of palladium and nickel (0.12% of palladium oxide, and 8% of nickel oxide based on the percentage by weight of the catalyst, wherein the carrier was alumina) was used as the catalyst; the catalyst had an intensity of 120N/cm, a surface area of 160 m$^2$/g, a pore volume of 0.38 ml/g, and an average pore diameter of 5 nm; the ethylene glycol product prepared from the hydrogenation of the dimethyl oxalate was used as the raw material; hydrogen and the ethylene glycol raw material (the ethylene glycol raw material had a purity of 99.8%; the UV-light transmittance of said raw material was 10 at 220 nm, 88 at 275 nm, and 95 at 350 nm) were passed through the rotating packed bed reactor at a temperature of 80° C., a pressure of 0.5 MPa, a space velocity of 15 hr$^{-1}$, and a ratio of hydrogen to ethylene glycol of 15:1 and contacted with the catalyst. The effluent of ethylene glycol was obtained after the reaction, wherein the rotation rate of the rotating packed bed reactor was 1000 rpm, and the UV-light transmittance of the ethylene glycol products obtained after the hydrogenation was 81 at 220 nm, 96 at 275 nm and 100 at 350 nm.

Comparative Example 1

The same catalyst, raw materials and reaction conditions as those in Example 6 were used, except that the reactor was a fixed bed tubular reactor. The UV-light transmittance of the ethylene glycol products obtained after the hydrogenation was 50 at 220 nm, 92 at 275 nm and 99 at 350 nm.

Comparative Example 2

The same catalyst, raw materials and reaction conditions as those in Example 7 were used, except that the reactor was a fixed bed tubular reactor. The UV-light transmittance of the ethylene glycol products obtained after the hydrogenation was 60 at 220 nm, 93 at 275 nm and 99 at 350 nm.

Therefore, from the above examples, it can be obviously seen that the present invention has achieved the technical effect as described.

The invention claimed is:

1. A method for improving quality of ethylene glycol products, wherein ethylene glycol raw material obtained by hydrogenation of oxalates and hydrogen are passed through a rotating packed bed reactor loaded with a solid oxide catalyst at a temperature of about 20 to about 280° C., a pressure of about 0.1 to about 4.0 MPa, a space velocity of about 0.2 to about 100.0 hr$^{-1}$ and a molar ratio of hydrogen to ethylene glycol of from about 0.01:1 to about 40:1, and ethylene glycol is obtained after the reaction, wherein said solid oxide catalyst is at least one of copper-based, nickel-based and palladium-based catalysts, and a rotation rate of said rotating packed bed reactor is about 300 to about 5000 rpm.

2. The method according to claim 1, wherein the temperature is about 30 to about 260° C., the pressure is about 0.3 to about 3.0 MPa, the space velocity is about 1 to about 50.0 hr$^{-1}$, and the molar ratio of hydrogen to ethylene glycol is from about 0.1:1 to about 30:1.

3. The method according to claim 1, wherein the rotation rate of the rotating packed bed reactor is about 500 to about 3000 rpm.

4. The method according to claim 1, wherein a mass concentration of the ethylene glycol raw material is greater than 99%.

5. The method according to claim 1, wherein said solid oxide catalyst has an intensity of about 60 to about 400N/cm.

6. The method according to claim 1, wherein said solid oxide catalyst have the following parameters: a surface area of about 10 to about 500 m$^2$/g, a pore volume of about 0.1 to about 1 ml/g, and a mean pore diameter of about 2 to about 13 nm.

7. The method according to claim 1, wherein said solid oxide catalyst is a catalyst comprising palladium oxide and/or copper oxide and/or nickel oxide.

8. The method according to claim 1, wherein said solid oxide catalyst comprises a carrier and optionally an adjuvant.

9. The method according to claim 1, wherein said ethylene glycol obtained immediately after the reaction has UV-light transmittances at 220 nm of greater than 75, at 275 nm of greater than 95 and at 350 nm of greater than 98.

10. The method according to claim 9, wherein said ethylene glycol obtained immediately after the reaction has UV-light transmittances at 275 nm of 96 or more, or at 350 nm of 99 or more.

11. The method according to claim 9, wherein said ethylene glycol obtained immediately after the reaction has UV-light transmittances at 275 nm of 97 or more, or at 350 nm of 100.

12. The method according to claim 1, wherein said ethylene glycol raw material obtained by hydrogenation of oxalates has UV-light transmittances at 220 nm of from 0 to 10, at 275 nm of from 88 to 93 and at 350 nm of from 93 to 95.

13. The method according to claim 12, wherein said ethylene glycol obtained immediately after the reaction has UV-light transmittances at 220 nm of from 76 to 81, at 275 nm of 95 to 97 and at 350 nm of 99 to 100.

14. The method according to claim 1, wherein said ethylene glycol is obtained immediately after the reaction.

* * * * *